(12) United States Patent
Partridge et al.

(10) Patent No.: US 12,092,634 B2
(45) Date of Patent: Sep. 17, 2024

(54) METHODS FOR QUANTIFYING IL-33

(71) Applicant: Regeneron Pharmaceuticals, Inc., Tarrytown, NY (US)

(72) Inventors: Michael Partridge, Eastchester, NY (US); Giane Oliveira Sumner, Mahwah, NJ (US); Joshua Zylstra, South Kent, CT (US)

( * ) Notice: Subject to any disclaimer, the term of this patent is extended or adjusted under 35 U.S.C. 154(b) by 538 days.

(21) Appl. No.: 17/046,200

(22) PCT Filed: Apr. 10, 2019

(86) PCT No.: PCT/US2019/026699
§ 371 (c)(1),
(2) Date: Oct. 8, 2020

(87) PCT Pub. No.: WO2019/199910
PCT Pub. Date: Oct. 17, 2019

(65) Prior Publication Data
US 2021/0033600 A1  Feb. 4, 2021

Related U.S. Application Data

(60) Provisional application No. 62/655,887, filed on Apr. 11, 2018.

(51) Int. Cl.
*G01N 33/53* (2006.01)
*G01N 33/68* (2006.01)

(52) U.S. Cl.
CPC ..... *G01N 33/5306* (2013.01); *G01N 33/6869* (2013.01); *G01N 2333/54* (2013.01)

(58) Field of Classification Search
CPC ........... G01N 33/5306; G01N 33/6869; G01N 2333/54; G01N 33/54393
See application file for complete search history.

(56) References Cited

U.S. PATENT DOCUMENTS 7,452,980 B2   11/2008   Kingsbury et al.
8,187,596 B1   5/2012   Chackerian et al.
(Continued)

FOREIGN PATENT DOCUMENTS

EP   1725261 A2   11/2006
WO   2005/079844 A2   9/2005
(Continued)

OTHER PUBLICATIONS

Zhu et al (Alignment of Non-Covalent Interactions at Protein-Protein Interfaces, PLoS One. 2008; 3(4): e1926.) (Year: 2008).*
(Continued)

*Primary Examiner* — Ann Montgomery
*Assistant Examiner* — Chau N. B. Tran
(74) *Attorney, Agent, or Firm* — McCarter & English, LLP; John P. Isacson; Alexa Marie J. Derkasch

(57) ABSTRACT

Methods and compositions for detecting and quantifying cytokines are provided. The disclosed assays have reduced assay interference relative to commercially available assays and/or a control assay. The interference can be cytokine dependent, cytokine independent, or both. One embodiment provides an IL-33 immunoassay that reduces assay interference caused by endogenous soluble IL-33 binding molecules present in the sample. Exemplary soluble IL-33 binding molecules include, but are not limited to anti-IL-33 antibodies, soluble ST2 receptor, and serum components. In some embodiments a blocking agent is added to the sample to reduce, inhibit, or block IL-33 complexes in the sample from reforming after acid dissociation of the IL-33 complexes in the sample. In one embodiment, the blocking agent and the detection reagent do not compete for binding to IL-33.

30 Claims, 8 Drawing Sheets

(56) References Cited

U.S. PATENT DOCUMENTS

| | | | |
|---|---|---|---|
| 8,263,415 B2* | 9/2012 | Berling | G01N 33/54393 435/7.1 |
| 8,444,987 B2 | 5/2013 | Kingsbury et al. | |
| 9,309,319 B2* | 4/2016 | Fertig | C07K 16/2866 |
| 9,453,072 B2 | 9/2016 | Murphy et al. | |
| 9,637,535 B2 | 5/2017 | Murphy et al. | |
| 9,758,578 B2 | 9/2017 | Fujino et al. | |
| 9,759,732 B2* | 9/2017 | Grabert | G01N 33/6854 |
| 9,951,137 B2 | 4/2018 | Fursov et al. | |
| 9,970,944 B2 | 5/2018 | Schmitz et al. | |
| 9,982,054 B2 | 5/2018 | Smith et al. | |
| 10,000,564 B2 | 6/2018 | Murphy et al. | |
| 10,059,764 B2 | 8/2018 | King et al. | |
| 10,093,730 B2 | 10/2018 | Hass et al. | |
| 10,815,305 B2* | 10/2020 | Orengo | C07K 16/2866 |
| 11,059,895 B2* | 7/2021 | Smith | A61P 11/00 |
| 2016/0168242 A1 | 6/2016 | Hass et al. | |
| 2017/0311580 A1 | 11/2017 | Wang et al. | |
| 2018/0037644 A1 | 2/2018 | Bloom et al. | |
| 2018/0155436 A1 | 6/2018 | Orengo et al. | |
| 2018/0171405 A1 | 6/2018 | Khosla et al. | |
| 2018/0207265 A1 | 7/2018 | Lowe et al. | |

FOREIGN PATENT DOCUMENTS

| | | |
|---|---|---|
| WO | 2011/031600 A1 | 3/2011 |
| WO | 2012/085228 A1 | 6/2012 |
| WO | 2012/113813 A1 | 8/2012 |
| WO | 2013/165894 A2 | 11/2013 |
| WO | 2013/173761 A2 | 11/2013 |
| WO | 2014/152195 A1 | 9/2014 |
| WO | 2015/099175 A1 | 7/2015 |
| WO | 2015/106080 A2 | 7/2015 |
| WO | 2016/077366 A1 | 5/2016 |
| WO | 2016/156440 A1 | 10/2016 |

OTHER PUBLICATIONS

Zhou et al (Synthesis, labeling and bioanalytical applications of a tris(2,2'-bipyridyl) ruthenium (II)-based electrochemiluminescence probe, Nature Protocols vol. 9, pp. 1146-1159 (2014)) (Year: 2014).*

Ketelaar et al (The challenge of measuring IL-33 in serum using commercial ELISA: lessons from asthma, Clin Exp Allergy, Jun. 2016;46(6):884-7. doi: 10.1111/cea.12718.) (Year: 2016).*

Zoghbi (A breakthrough novel method to resolve the drug and target interference problem in immunogenicity assays, J Immunol Methods, Nov. 2015;426:62-9. doi: 10.1016/j.jim.2015.08.002. Epub Aug. 6, 2015.) (Year: 2015).*

Quantikine ELISA (Human IL-33 Immunoassay) (Year: 2015).*

Tate et al (Interferences in Immunoassay, Clin Biochem Rev. May 2004; 25(2): 105-120.) IDS #15 (Year: 2004).*

G-Biosciences (ELISA Blocking Agents & Blocking Solutions, 2017) (Year: 2017).*

Salimi-Moosavi et al (Novel approaches using alkaline or acid/guanidine treatment to eliminate therapeutic antibody interference in the measurement of total target ligand, 2010) (Year: 2010).*

Bird et al., "Single-chain antigen-binding proteins," Science, 242(4877):423-426 (1988).

Dai et al., "Development of a Method That Eliminates False-Positive Results due to Nerve Growth Factor Interference in the Assessment of Fulranumab Immunogenicity," The AAPS Journal, 16(3): 464-477 (2014).

Doucet et al., "Development and Validation of an ELISA at Acidic pH for the Quantitative Determination of IL-13 in Human Plasma and Serum," Disease Markers, 77(8): 1627-474 (2013).

Holliger et al., ""Diabodies": small bivalent and bispecific antibody fragments," Proc. Natl. Acad Sci. USA, 90:6444-6448 (1993).

Hong et al., "Identification of Constitutively Active Interleukin 33 (IL-33) Splice Variant," J. Biol. Chem., 286(22):20078-20086 (2011).

Huston et al., "Protein engineering of antibody binding sites: recovery of specific activity in an anti-digoxin single-chain Fv analogue produced in *Escherichia coli*," Proc. Natl. Acad. Sci. USA, 85:5879-5883 (1988).

International Preliminary Report on Patentability received for PCT Patent Application No. PCT/US2019/026699, mailed on Oct. 22, 2020, 9 pages.

International Search Report and Written Opinion received for PCT application PCT/US19/26699, mailed on Jul. 8, 2019, 17 pages.

Ketelaar et al., "The challenge of measuring IL-33 in serum using commercial ELISA: lessons from asthma," Clinical & Experimental Allergy: Journal of the British Society for Allergy and Clinical Immunology, 46(6): 884-887 (2016).

Kim et al., "Development of an interleukin (IL)-33 sandwich ELISA kit specific for mature IL-33," Journal of Immunoassay and Immunochemistry, 37(6): 585-596 (2016).

Lofgren et al., "Comparing ELISA and surface plasmon resonance for assessing clinical immunogenicity of pantiumumab," The Journal of Immunology, The American Association of Immunologists, 178(11): 7567-7472 (2007).

Nygaard et al., "Measuring serum concentrations of interleukin-33 in atopic dermatitis is associated with potential false positive results," Springerplus, Biomed Central LTD, London, UK, 5(1): 1-4 (2016).

Riviere et al., Pitfalls for detecting interleukin-33 by ELISA in the serum of patients with primary Sjogren syndrome: comparison of different kits, Annals of the Rheumatic Diseases, vol. 75, No. 3, Mar. 10, 2016, pp. 633-635.

Schwickart et al, "Interference in immunoassays to support therapeutic antibody development in preclinical and clinical studies," Bioanalysis, 6(14): 1939-1951 (2014).

Tate et al., "Interferences in immunoassay," Clin. Biochem. Rev., 25(2): 105-120 (2004).

Verch et al., "Pharmacokinetic immunoassay methods in the presence of soluble target," Journal of Immunological Methods, 361(1): 75-81 (2010).

Ward et al., "Binding activities of a repertoire of single immunoglobulin variable domains secreted from *Escherichia coli*," Nature, 241:544-546 (1989).

Zhong et al., "Drug Target Interference in Immunogenicity Assays: Recommendations and Mitigation Strategies," AAPS J., 19(6): 1564-1575 (2017).

Zoghbi et al, "A breakthrough novel method to resolve the drug and target interference problem in immunogenicity assays," Journal of Immunological Methods, 426: 62-69 (2015).

Lakshman, K.M., et al., "Measurement of myostatin concentrations in human serum: Circulating concentrations in young and older men and effects of testosterone administration," Molecular and Cellular Endocrinology, 302: 26-32. (2009).

* cited by examiner

METHODS FOR QUANTIFYING IL-33

CROSS REFERENCE TO RELATED APPLICATIONS

This application is a national stage application, filed under 35 U.S.C. § 371, of International Patent Application No. PCT/US2019/026699 filed on Apr. 10, 2019, which claims benefit of and priority to U.S. Provisional Patent Application No. 62/655,887, filed on Apr. 11, 2018, and which are incorporated herein by reference in their entirety.

TECHNICAL FIELD OF THE INVENTION

Aspects of the invention are generally related to immunoassays for the detection and quantification of cytokines, including but not limited to interleukin 33 (IL-33).

BACKGROUND OF THE INVENTION

Interleukin 33 (IL-33) is a cytokine that is unregulated in response to damage signals or insults, such as cigarette smoke. It is released by barrier tissues upon necrosis and propagates an immune response to the presence of damaged tissue. This "alarmin" signal amplifies inflammatory responses for both innate and adaptive immunity. Published data indicate that commercial kits for detecting soluble IL-33 generate unreliable results, probably due to interference from endogenous binding partners, such as soluble ST2 receptor (Nygaard, U., et al., SpringerPlus, 5:33 (2016); Ketelaar, M. E., Clin Exp Allergy, 46(6):884-7 (2016); Rivière, E. et al., Ann Rheum Dis, 75(3):633-5 (2016)).

The performance of ligand binding assays in complex matrices, such as serum, can be impacted by specific endogenous components interfering with the assay (Zhong, Z. D., et al., AAPS J, 19: 1564 (2017)). Interference in an immunoassay may lead to the misinterpretation of a patient's results by the laboratory and the wrong course of treatment being given by the physician (Tate, J., et al., Clin Biochem Rev. 2004, 25(2): 105-120).

Attempts to develop better immunoassays have been attempted by others. Doucet, J. et al. reported an improved IL-13 assay that included an acid disassociation step (Doucet, J. et al., Disease Markers, 35(5):465-474 (2013)). The immunoassay described by Doucet is specific for IL-13 and did not detect IL-33. Additionally, Doucet's immunoassay did not require neutralizing the sample prior to detection and did not use a blocking agent to prevent cytokine complex reformation during the assay.

Therefore there is a need for new assays and methods for the detection of IL-33.

SUMMARY OF THE INVENTION

Methods and compositions for detecting and quantifying cytokines are provided. The disclosed assays have reduced assay interference relative to commercially available assays and/or a control assay. The interference can be cytokine dependent, cytokine independent, or both. One embodiment provides an IL-33 immunoassay that reduces assay interference caused by endogenous soluble IL-33 binding molecules present in the sample. Exemplary soluble IL-33 binding molecules include, but are not limited to anti-IL-33 antibodies, soluble ST2 receptor, and serum components. In some embodiments a blocking agent is added to the sample to reduce, inhibit, or block IL-33 complexes in the sample from reforming after acid dissociation of the IL-33 complexes in the sample. In one embodiment, the blocking agent and the detection reagent do not compete for binding to IL-33.

Another embodiment provides methods to determine the concentration of total IL-33 in human serum samples using an electrochemiluminescence immunoassay. The assay includes acid pre-treatment of serum samples to dissociate soluble ligand:drug complexes present in the samples and improve detection of IL-33 in the presence of drug, thus providing a quantitative measurement of the levels of total IL-33. In this embodiment the procedure employs a streptavidin-coated plate, with a biotinylated anti-human IL-33 antibody as the capture reagent, and utilizes recombinant IL-33 as a standard. The standards, controls, and samples are diluted in acetic acid and neutralized using a Tris-base solution containing the detection reagent, for example a ruthenium-labeled antihuman IL-33 antibody. An antibody that binds to anti-IL-33 antibody and an anti-ST2 receptor antibody are also added to the Tris solution to minimize interference from the drug (i.e., antibody that bind antibodies to IL-33) or endogenous soluble ST2 receptor. Neutralized standards, controls, and samples are then added to the plate. IL-33 captured on the plate is measured by a chemiluminescent signal generated by the ruthenium label when voltage is applied to the plate by the plate reader. The resulting electrochemiluminescent signal (i.e., Counts) is proportional to the amount of IL-33 present in the serum samples.

In one embodiment, the method has a sensitivity of 12.5 pg/mL and an ST2 tolerance of >50 ng/mL.

DETAILED DESCRIPTION OF THE INVENTION

I. Definitions

Figure 1:
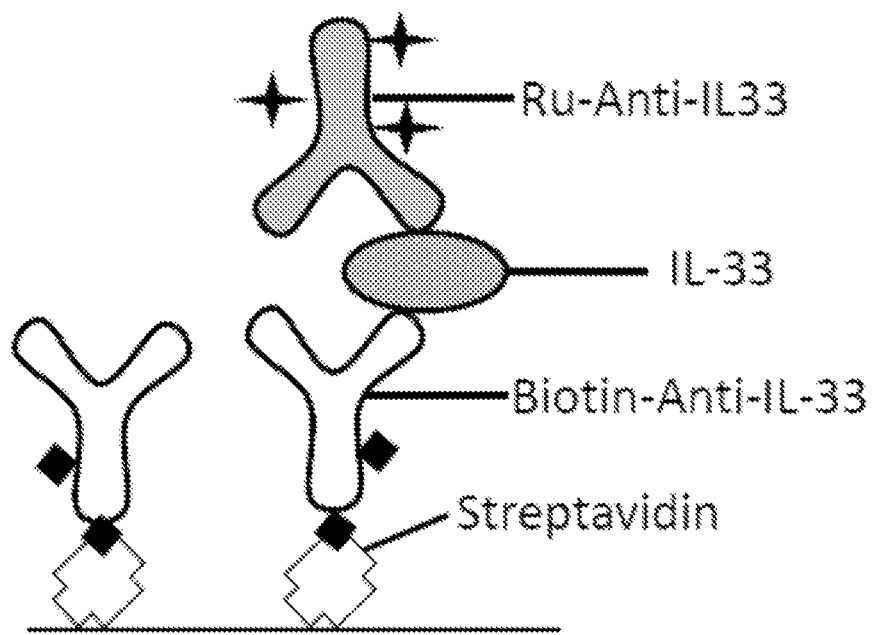
FIG. 1 is a diagram of an exemplary assay scheme according to one embodiment of the invention. ✦—ruthenium label, ■—biotin, ○—streptavidin

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The term "binding molecule," as used herein is intended to refer to molecules that specifically interact with and bind to a particular target. The target can comprise a biologic or small (chemical) molecule. The target molecule may define an antigen or antigenic moiety. Examples of a binding molecule include, but are not limited to, antibodies (including monoclonal antibodies, bispecific antibodies, as well as antibody fragments), fusion proteins, and other antigen-binding molecule known to those skilled in the art.

The term "antibody," as used herein, is an example of a binding molecule and refers to an immunoglobulin that typically comprises four polypeptide chains, two heavy (H) chains and two light (L) chains inter-connected by disulfide bonds. Each heavy chain comprises a heavy chain variable region (HCVR or $V_H$) and a heavy chain constant region. The heavy chain constant region comprises three domains, $C_H1$, $C_H2$ and $C_H3$. Each light chain contains a light chain variable region (LCVR or $V_L$) and a light chain constant region. The light chain constant region comprises one domain ($C_L1$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or simply "antibody portion" or "antibody fragment"), as used herein, refers to one or more fragments of an antibody that retain the ability to specifically bind to an antigen (e.g., hIL-33). It has been shown that the antigen-binding function of an antibody can be performed by fragments of a full-length antibody. Examples of binding fragments encompassed within the term "antigen-binding portion" of an antibody include (i) a Fab fragment, a monovalent fragment comprising the $V_L$, $V_H$, $C_L1$ and $C_H1$ domains; (ii) a F(ab')$_2$ fragment, a bivalent fragment comprising two F(ab)' fragments linked by a disulfide bridge at the hinge region; (iii) a Fc fragment comprising the $V_H$ and $C_H1$ domains; (iv) a Fv fragment comprising the $V_L$ and $V_H$ domains of a single arm of an antibody, (v) a dAb fragment (Ward, E. S., et al., Nature 241:544-546 (1989)), which comprises a VH domain; and (vi) a CDR. Furthermore, although the two domains of the Fv fragment, $V_L$ and $V_H$, are coded for by separate genes, they can be joined, using recombinant methods, by a synthetic linker that enables them to be made as a single contiguous chain in which the $V_L$ and $V_H$ regions pair to form monovalent molecules (known as single chain Fv (scFv); see e.g., Bird, R. E., et al., Science 242:423-426 (1988); and Huston, J. S., et al., Proc. Natl. Acad. Sci. USA 85:5879-5883 (1988)). Such single chain antibodies are also intended to be encompassed within the term "antigen-binding portion" of an antibody. Other forms of single chain antibodies, such as diabodies, are also encompassed (see e.g., Holliger, P., et al., Proc. Natl. Acad Sci. USA 90:6444-6448 (1993)).

A "CDR" or complementarity determining region is a region of hypervariability interspersed within regions that are more conserved, termed "framework regions" (FR). The FRs may be identical to the human germline sequences, or may be naturally or artificially modified.

The term "epitope" is an antigenic determinant that interacts with a specific antigen binding site in the variable region of an antibody molecule known as a paratope. A single antigen may have more than one epitope. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstances, an epitope may include moieties of saccharides, phosphoryl groups, or sufonyl groups on the antigen.

The term "assay interference" refers to endogenous components in the assay that block or inhibit detection of the analyte, such as IL-33 or an anti-IL-33 antibody. Substances that alter the measurable concentration of the analyte or alter antibody binding can potentially result in immunoassay interference. Assay interference may be analyte-dependent or—independent. Analyte-independent interferences refer to the common interferences of hemolysis, lipemia and effects of anticoagulant and sample storage, and are independent of the analyte concentration. Analyte-dependent interferences in immunoassays refer to interaction between constituents in the sample with one or more reagent antibodies. They include compounds with chemical differences but structural similarities that cross-react with the antibody. Interfering, endogenous substances that are natural, polyreactive antibodies or autoantibodies (heterophiles), human anti-animal antibodies, or anti-drug antibodies (ADAs) together with other unsuspected binding proteins that are unique to the individual, can interfere with the reaction between analyte and reagent antibodies in an immunoassay. Interference can be caused by soluble binding targets of the analyte, endogenous ligands of the analyte including but not limited to soluble receptors of the analyte, soluble ligands of the analyte, shed receptors of the analyte, or serum factors such as rheumatoid factor and biotin. Interference can be caused by antibodies to the analyte.

The term "ST2" refers to the receptor for IL-33 which is also referred to as Interleukin-1-receptor-like-1 (IL-1RL1). ST2 can be membrane bound or soluble.

The term "immunoassay" refers to a detection assay that incorporates a binding moiety that immunospecifically binds directly or indirectly to an analyte. Typically the binding moiety is an antibody. The antibody can be labeled with a detectable label.

The term "IL-33 complex" refers to the non-covalent association of IL-33 with a component of blood, plasma, or serum. Typically, the IL-33 complex contains IL-33 non-covalently bound to a protein, for example a protein drug product, an anti-drug antibody, a ligand of IL-33 or a combination thereof.

II. IL-33 Detection and Quantification Assays and Methods of Use Thereof

Assays and methods for the detection and quantification of IL-33 are provided. The disclosed assays and methods can be used to detect and quantify IL-33 in a sample. In one embodiment, the sample is obtained from subject treated or being treated with an IL-33 antagonist or with IL-33.

The disclosed assays have reduced assay interference relative to commercially available assays and/or a control assay. The interference can be IL-33 dependent, IL-33 independent, or both. In one embodiment the method reduces or inhibits assay interference caused by endogenous soluble IL-33 binding molecules present in the sample. Exemplary soluble IL-33 binding molecules include, but are not limited to anti-IL-33 antibodies, soluble ST2, and serum components. In some embodiments a blocking agent is added to the sample to reduce, inhibit, or block IL-33 complexes in the sample from reforming after acid denaturation of the IL-33 complexes in the sample. In one embodiment, the blocking agent and the detection reagent do not compete for binding to IL-33.

In one embodiment, the method has a sensitivity of 12.5 pg/mL and an ST2 tolerance of >50 ng/mL.

A. Interleukin 33

In one embodiment, IL-33 or "human interleukin-33" or "human IL-33" refers to the 270 amino acid, full-length, unprocessed IL-33 (See, for example UniProtKB accession number O95760 and US Patent Application Pub. No. 20180155436, both of which are incorporated by reference in their entireties), or a biologically active fragment thereof, as well as any form of IL-33 that results from processing in the cell. The term also encompasses naturally occurring variants of IL-33, for example, splice variants (See for example, Hong, et. al., (2011), J. Biol. Chem. 286(22): 20078-20086), or allelic variants, or any other isoform of IL-33, such as the oxidized or reduced forms of IL-33 described in WO2016/156440. The activity of IL-33 that can be neutralized, inhibited, blocked, abrogated, attenuated, reduced or interfered with, by an antibody or antigen-binding fragment thereof, or by an IL-33 trap, includes, but is not limited to, inhibition of IL-33 receptor-mediated signaling, or inhibition of IL-33-mediated inflammation.

B. Methods for Detecting IL-33

One embodiment provides a method of detecting IL-33 in a sample by acidifying the sample to a pH sufficient to dissociate IL-33 complexes in the sample and neutralizing the acidified sample with a buffered base solution. Capture and detection reagents are also added to the sample to detect IL-33. In certain embodiments, a blocking agent is added to the sample to inhibit, reduce, or block components in the sample from binding IL-33.

Another embodiment provides a method of decreasing assay interference by acidifying a sample to a pH sufficient to dissociate IL-33 from IL-33 complexes in the sample, and subsequently neutralizing the acidified sample with a buffered basic solution containing a detection reagent. Optionally, a blocking agent that inhibits the IL-33 complexes from reforming in the sample can be added to the sample in a separate step or can be present in the buffered basic solution. The method includes adding a capture reagent to the sample and detecting the detection agent, wherein the quantity of detection reagent detected correlates to the quantity of IL-33 in the sample. The capture agent can be added as a separate step or can be present in the acidifying step or in the buffered basic solution. Typically, the IL-33 complexes present in the sample contain IL-33 non-covalently associated with soluble ST2.

Another embodiment provides a method of quantifying interleukin-33 in a serum sample by acidifying the serum sample to a pH sufficient to dissociate IL-33 complexes in the sample, and subsequently neutralizing the acidified sample with a buffered basic solution containing (a) an anti-human IL-33 antibody labeled with a detectable label, and optionally (b) an anti-human ST2 antibody. The method includes adding the sample to a streptavidin-coated solid support containing a biotinylated anti-human IL-33 antibody, and detecting the detectable label on the avidin-coated solid support, wherein the quantity of detectable label detected correlates to the quantity of IL-33 in the sample.

Another embodiment provides a method to determine the concentration of total IL-33 in human serum samples using an electrochemiluminescence immunoassay. The assay includes acid pre-treatment of serum samples to dissociate soluble ligand:drug complexes present in the samples and improve detection of IL-33 in the presence of drug, thus providing a quantitative measurement of the levels of total IL-33. Ligand: drug complexes include, but are not limited to IL-33 non-covalently bound to an anti-IL-33 antibody. An exemplary anti-IL-33 antibody is disclosed in U.S. Pat. Nos. 10,000,564 and 9,453,072, which are incorporated by reference in their entirety. In this embodiment the procedure employs a streptavidin-coated plate, with a biotinylated antihuman IL-33 antibody as the capture reagent, and utilizes recombinant IL-33 as a standard. The standards, controls, and samples are diluted in acetic acid and neutralized using a Tris-base solution containing the detection reagent, for example a ruthenium-labeled antihuman IL-33 antibody. An antibody that binds to an anti-IL-33 antibody and an anti-ST2 receptor antibody are also added to the Tris solution to minimize interference from the drug or endogenous soluble ST2 receptor. Neutralized standards, controls, and samples are then added to the plate. IL-33 captured on the plate is measured by a chemiluminescent signal generated by the ruthenium label when voltage is applied to the plate by the plate reader. The resulting electrochemiluminescent signal (i.e., Counts) is proportional to the amount of IL-33 present in the serum samples.

In one embodiment, the amount of label detected in the sample is compared to a reference standard calibrated with known concentrations of IL-33 and corresponding amounts of detected label for the concentrations. The amount of IL-33 in the sample can be determined by comparing the amount of detected label in the sample to the reference standard and matching the amount of detected label with the concentration shown on the reference standard for that amount of detected label.

1. Biologic Samples

The sample used in the disclosed methods is typically a biological sample such as a biological fluid containing the analyte to be detected, for example IL-33 or a complex thereof. Biological fluids include, but are not limited to blood, plasma, serum and saliva. In a preferred embodiment, the biological sample is a human biological sample.

In certain embodiments, the sample is obtained from a subject having or suspected of having an inflammatory condition, disease, or disorder. Representative inflammatory conditions, diseases, and disorders include but are not limited to Crohn's disease, colitis, ulcerative colitis, atopic dermatitis, asthma, allergic rhinitis, allergic conjunctivitis, eosinophilic esophagitis, nasal polyps or a combination thereof.

The analyte to be detected is typically a component of serum taken from a subject, preferably a human subject. Representative analytes to be detected and/or quantified in the sample include, but are not limited to cytokines, protein drug products, and metabolites or fragments thereof.

Representative cytokines include interleukins. Interleukins include IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, and IL-36. In one embodiment, the analyte is IL-33.

Representative protein drug products include, but are not limited to recombinant proteins, antibodies, and fusion proteins. The antibodies can be polyreactive antibodies or autoantibodies (heterophiles), human anti-animal antibodies, or anti-drug antibodies. In one embodiment, the protein drug product is an anti-IL-33 antibody.

2. Ligands of IL-33

Ligands of IL-33 are molecules that non-covalently bind to IL-33 and include but are not limited to endogenous components in the sample such as antibodies or soluble binding targets of the analyte, endogenous ligands of IL-33 including but not limited to soluble receptors of IL-33, soluble ligands of IL-33, and shed receptors of the analyte. In one embodiment, the ligand of IL-33 is soluble ST2 receptor or soluble coreceptor IL-1 receptor accessory protein (IL-1RAcP).

ST2 (also known as IL1RL1, DER4, T1 and FIT-1) is a member of the Toll-like/IL-1-receptor superfamily. Members of this superfamily are defined by a common intracellular domain, the Toll/Interleukin-1 receptor (TIR) domain. This domain of ~160 amino acids is composed of a central five-stranded β-sheet surrounded by five α-helices located on the cytosolic end of the protein. The Toll-like/IL-1-receptor superfamily can be divided into three subfamilies based on their extracellular domains: the IL-1 receptor-like subfamily, the Toll receptor subfamily and a family comprised of their adaptor proteins.

3. Acid Denaturation of IL-33 Complexes

The sample in the disclosed methods can be acidified for 1 to 60 minutes. In one embodiment the sample is acidified for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 minutes.

Acids that can be used in the acidification step include but are not limited to acetic acid, hydrochloric acid, and sulfuric acid.

The pH that is sufficient to dissociate IL-33 complexes can be from 3.0 to 5.0. In one embodiment the pH is 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

In one embodiment a denaturing agent can be added to the sample to dissociate the IL-33 complexes including, but not limited to urea.

4. Blocking Agent

The blocking agent used in the disclosed methods is an agent that reduces or prevents the reformation of IL-33 complexes in the sample after the IL-33 complexes have been dissociated in the acidification step. When the sample is taken from a subject, for example a human subject, the sample typically contains IL-33 complexes to be detected or quantified. The blocking agent can be an antibody that immunospecifically binds to a component of an IL-33 complex other than IL-33. In one embodiment, the blocking agent is an anti-ST2 antibody.

In one embodiment, the blocking agent is an antibody that binds to an IL-33 drug product, for example an antibody that binds to an anti-IL-33 antibody.

5. Detection Reagent

The detection reagent used in the disclosed methods can be an IL-33 antagonist or inhibitor, for example an anti-IL-33 antibody, preferably an anti-human IL-33 antibody or an IL-33 trap. The antibody can be monoclonal, polyclonal, or humanized.

In some embodiments, the detection reagent is labeled with a detectable label. Detectable labels are known in the art and include, but are not limited to a rare transition metal particle, a fluorophore, a chromophore, a quantum dot, noble metal nanoparticles, a radioactive moiety, an enzyme, a biotin/avidin label, and a chemiluminescent label. In one embodiment, the detectable label is ruthenium.

a. Anti-IL-33 Antagonists

In certain embodiments, IL-33 antagonists or inhibitors that can be used in the disclosed assays and methods are anti-IL-33 antibodies or antigen-binding fragments of antibodies that specifically bind human IL-33. In one embodiment, the anti-IL-33 antibodies described herein for use in the disclosed methods and assays are disclosed in U.S. Pat. Nos. 10,000,564 and 9,453,072, which are incorporated by reference in their entirety.

The anti-IL-33 antibodies used in the disclosed assays and methods specifically bind to IL-33. The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-33 as used herein, includes antibodies that bind to IL-33 or a biologically active portion thereof with a $K_D$ of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human IL-33 may, however, have cross-reactivity to other antigens, such as IL-33 molecules from other (non-human) species.

In some embodiments, the IL-33 antagonist is an anti-IL-33 antibody, or antigen-binding fragment thereof comprising a heavy chain variable region (HCVR), light chain variable region (LCVR), and/or complementarity determining regions (CDRs) comprising any of the amino acid sequences of the anti-IL-33 antibodies as set forth in U.S. Pat. Nos. 10,000,564 and 9,453,072. In certain embodiments, the IL-33 antagonist is an anti-IL-33 antibody having the binding characteristics of the reference antibody described in U.S. Pat. Nos. 10,000,564 and 9,453,072.

Other anti-IL-33 antibodies and antigen-binding fragments thereof that may be used in the methods described herein are disclosed in EP1725261 and U.S. Pats. No. 9,970,944, 8,187,596, WO2011031600, WO2015099175 and U.S. Pat. No. 9,758,578, WO2015106080 and U.S. Pat. No. 10,059,764 (ANB020), US2016/0168242, WO2016/077381 and U.S. Pat. No. 10,093,730, WO2016/077366 and US2018/0171405, or WO2016/156440 and US2018/0207265, which are each incorporated herein by reference in their entirety.

b. IL-33 Traps

In some embodiments, IL-33 antagonists or inhibitors that can be used in the disclosed methods and assays are receptor based IL-33 traps. Exemplary IL-33 traps include at least one IL-33 binding domain containing an IL-33 binding portion of an IL-33 receptor protein, for example ST2. In certain embodiments the IL-33 trap further includes an extracellular portion of an IL-33 co-receptor, for example IL-1 receptor accessory protein, or IL-1RAcP. The IL-33 trap may also contain at least one multimerizing component which functions to connect the various components of the trap with one another.

In one embodiment, the IL-33 traps described herein for use in the disclosed methods and assays are disclosed in U.S. Pat. No. 9,637,535 and WO2014/152195, which are each incorporated herein by reference in their entirety.

Generally, an IL-33 trap includes a first IL-33 binding domain (D1) attached to a multimerizing domain (M). In certain embodiments, the IL-33 antagonists include a second IL-33 binding domain (D2) attached to D1 and/or M. According to certain embodiments, D1 includes an IL-33-binding portion of an ST2 protein. An IL-33-binding portion of an ST2 protein can include or consist of all or part of the extracellular domain of an ST2 protein. In certain embodiments, an ST2 protein is a human ST2 protein. A "human ST2 protein," as used herein, refers to an ST2 protein as shown in amino acids 1-556 of accession number NP_057316.3 which is incorporated by reference in its entirety. According to certain embodiments, D2 includes an extracellular portion of an IL-1RAcP protein.

The individual components of the IL-33 traps may be arranged relative to one another in a variety of ways that result in functional antagonist molecules capable of binding IL-33. For example, D1 and/or D2 may be attached to the N-terminus of M. In other embodiments D1 and/or D2 is attached to the C-terminus of M. In yet other embodiments, D1 is attached to the N-terminus of D2, and D2 is attached to the N-terminus of M, resulting in an in-line fusion, from N- to C-terminus, of an antagonist molecule represented by the formula D1-D2-M.

In certain embodiments, the IL-33 antagonists have two multimerizing domains, M1 and M2, wherein M1 and M2 are identical to one another. For example, M1 can be an Fc domain having a particular amino acid sequence, and M2 is an Fc domain with the same amino acid sequence as M1.

c. Other IL-33 Antagonists

Other agents that may act as IL-33 antagonists and which may be used in the disclosed methods and assays include immunoadhesins, peptibodies, soluble ST2, or derivatives thereof; anti-IL-33 receptor antibodies (e.g., anti-ST2 antibodies, for example, AMG-282 (Amgen) or STLM15 (Janssen) or any of the anti-ST2 antibodies described in WO2012/113813 and U.S. Pat. No. 9,309,319, WO2013/173761 and U.S. Pat. No. 9,982,054, WO2013/165894 and U.S. Pat. Nos. 9,951,137, 8,444,987, or 7,452,980, which are each incorporated herein by reference in their entirety. Other IL-33 antagonists for use in the disclosed methods and assays include ST2-Fc proteins, such as those described in WO2013/173761 and U.S. Pat. No. 9,982,054, or WO2013/165894 and U.S. Pat. No. 9,951,137, which are each incorporated herein by reference in their entirety.

6. Capture Reagent

In one embodiment, the capture reagent used in the disclosed methods and assays is an IL-33 antagonist as described above, for example an antibody, preferably an anti-IL-33 antibody, preferably an anti-human IL-33 antibody. An exemplary anti-IL-33 antibody is disclosed in U.S. Pat. No. 10,000,564, which is incorporated by reference in its entirety. Other anti-IL-33 antibodies that can be used are described above. In one embodiment the capture reagent is biotinylated.

In some embodiments, the capture reagent is fixed to or linked to a solid support. The solid support can be a microplate, for example a streptavidin-coated microplate.

In some embodiments, the capture reagent is the IL-33 antagonists described above.

C. Companion Diagnostic

In one embodiment, the disclosed methods and assays for detecting and quantifying IL-33 are used as a companion diagnostic method in conjunction with treatments designed to reduce circulating levels of IL-33 in a subject being treated or to elevate circulating levels of IL-33 in a subject being treated. The treatments can include the administration of an IL-33 antagonist or the administration of IL-33. Exemplary IL-33 antagonists are those described above and include, but are not limited to anti-IL-33 antibodies, anti-IL-33 fusion proteins, sST decoy receptors, or a combination thereof.

One embodiment provides a method of monitoring the treatment of an IL-33 related disease in a subject receiving treatments including the administration of an IL-33 antagonist as described above or the administration of IL-33. Representative diseases, disorders, or pathologies treated with an IL-33 inhibitor or IL-33, include but are not limited to asthma, eosinophilic or non-eosinophilic asthma, atopic dermatitis, chronic obstructive pulmonary disease (COPD), inflammatory bowel disease, Crohn's disease, colitis, ulcerative colitis, multiple sclerosis, arthritis, allergic rhinitis, atopic dermatitis, eosinophilic esophagitis, psoriasis, nasal polyps, Alzheimer's disease, atherosclerosis, myocardial infarction, ischemic stroke, and fibrotic conditions including but not limited to Dupuytren's disease, adhesive capsulitis, periarticular fibrosis, keloid orhypertrophic scars, endometriosis, abdominal adhesions, perineuralfibrosis, Ledderhose disease, Peyronie's disease, peritendinousadhesions, and periarticular fibrosis.

The methods and assays described herein can be used to assess, detect, or quantify circulating IL-33 levels in a subject before and following treatment of a subject with one or more pharmaceutical compositions containing an IL-33 antagonist as described above (e.g., particularly with a pharmaceutical related to a mechanism of action involving IL-33), with anti-inflammatory therapy, or by immunoabsorption therapy, or where IL-33 is assessed following such treatment and the concentration or the amount of IL-33 is compared against a predetermined level or against the level measured in the subject prior to treatment. An unfavorable concentration of amount of IL-33 observed following treatment confirms that the subject will not benefit from receiving further or continued treatment, whereas a favorable concentration or amount of IL-33 observed following treatment confirms that the subject will benefit from receiving further or continued treatment.

In one embodiment an unfavorable concentration of IL-33 detected by the disclosed methods and assays in a sample from a subject receiving a treatment incorporating an IL-33 inhibitor is a level of IL-33 the same or higher than the level measured in the subject prior to treatment. In one embodiment a favorable concentration of IL-33 detected by the disclosed methods and assays on a sample from a subject receiving a treatment incorporating an IL-33 inhibitor is a level of IL-33 that is lower than the level of IL-33 measured in a sample from the subject prior to treatment.

In another embodiment an unfavorable concentration of IL-33 detected using the disclosed methods and assays in a sample from a subject receiving a treatment incorporating IL-33 is a level that is lower than the level of IL-33 measured in a sample from the subject prior to treatment. In another embodiment a favorable concentration of IL-33 detected using the disclosed methods and assays in a sample from a subject receiving a treatment incorporating IL-33 is a level of IL-33 that is higher than the level of IL-33 measured in a sample from the subject prior to treatment.

The confirmation of circulating IL-33 levels assists with management of clinical studies, and provision of improved patient care.

III. Kits

A kit for assaying a test sample for the presence, amount or concentration of IL-33 (or a fragment thereof) in a test sample is also provided. The kit includes at least one component for assaying the test sample for IL-33 (or a fragment thereof) and instructions for assaying the test sample for IL-33 (or a fragment thereof).

In one embodiment, the kit includes a detection reagent as described above, a capture reagent as described above, a solid support, other reagents and written instructions for performing the assay. The detection reagent and the capture reagent can be the same or different IL-33 antagonists described above, such as a monoclonal antibody (or a fragment, a variant, or a fragment of a variant thereof), a fusion protein, an IL-33 trap, or an apatamer optionally immobilized on a solid phase.

The detection reagent is typically labeled with a detectable label such as a chemiluminescent label. The detection reagent can incorporate a detectable label as described herein, such as a fluorophore, a radioactive moiety, an enzyme, a biotin/avidin label, a chromophore, a chemiluminescent label, or the like, or the kit can include reagents for carrying out detectable labeling. The antibodies, calibrators and/or controls can be provided in separate containers or pre-dispensed into an appropriate assay format, for example, into microtiter plates. In one embodiment, the IL-33 detection reagent is labeled with ruthenium.

In some embodiments, the kit contains a biotin labeled capture reagent and a streptavidin coated solid support, for example a microtiter plate or electrochemiluminescence platform. In some embodiments, the capture reagent and the microtiter plate or electrochemiluminescence platform are provided in separate containers. In other embodiments, the kit contains a microtiter or electrochemiluminescence platform plate coated with the capture reagent. The kit also contains acid solutions and buffers as described above for treating the samples.

The kit can include a calibrator or control, e.g., isolated or purified IL-33. The kit can include at least one container (e.g., tube, microtiter plates or strips or electrochemiluminescence platform) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit includes all components, i.e., reagents, standards, buffers, diluents, etc., which are necessary to perform the assay. The instructions can be in paper form or computer-readable form.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme co-factors, enzyme substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine sample). Where appropriate, the kit optionally also can contain reaction vessels, mixing vessels, and other components that facilitate the preparation of reagents or the test sample. The kit can also include one or more instruments for assisting with obtaining a test sample, such as a syringe, pipette, forceps, measured spoon, or the like.

EXAMPLES

Example I

Assay Format

FIG. 1 is a diagram of an exemplary assay for detecting IL-33. This method for quantitating IL-33 is a sandwich immunoassay on an electrochemiluminescence platform. The procedure employs a streptavidin coated microplate and uses a biotinylated anti-IL-33 antibody as the capture reagent. The method includes acid pre-treatment of serum samples to dissociate soluble ligand:binding partners complexes present in the samples and improve detection of IL-33 in the presence of binding partners, e.g. Anti-IL-33 therapeutic drug and/or soluble ST2, thus providing a quantitative measurement of the levels of total IL-33. The acidified samples were then neutralized in a basic solution containing a labeled anti-IL-33 detection antibody, which in one embodiment may compete with soluble ST2 receptor and drug for binding to IL-33.

Exemplary acids that can be used include, but are not limited to acetic acid, sulfuric acid, and hydrochloric acid. The sample can be neutralized using buffered basic solution, for example a Tris solution.

An exemplary IL-33 antibody that can be used is described in U.S. Pat. No. 10,000,564, which is incorporated by reference in its entirety. Other anti-IL-33 antibodies that can be used in the disclosed methods include, but are not limited to those described in U.S. Pat. No. 9,758,578 and US Patent Application Publication 2018/0037644.

In one embodiment the standards, controls, and samples are diluted in acetic acid and neutralized using a Tris-base solution containing the detection reagent, for example a ruthenium-labeled anti-human IL-33 antibody. An anti-IL-33 antibody and an anti-ST2 antibody are also added to the Tris solution to minimize interference from the drug or endogenous binding partners. Neutralized standards, controls, and samples are then added to the plate. IL-33 captured on the plate is measured by a chemiluminescent signal generated by the ruthenium label when voltage is applied to the plate by the plate reader. The resulting electrochemiluminescent signal (i.e., Counts) is proportional to the amount of IL-33 present in the serum samples.

Example II

Minimizing Endogenous Binding Partner Interference

Materials and Methods

Recombinant human ST2 tolerance was tested using 4 different conditions of the assay (described below), with the first (capture) step for all conditions being the addition of biotinylated anti-IL-33 mAb to a streptavidin plate.

For the assay performed in a stepwise progression (Capture-Analyte-Detection, C-A-D), the samples (containing the analyte, IL-33) were first diluted in an acidic solution and allowed to incubate. After plate washing, the acidified samples were then further diluted in a basic neutralization buffer before addition to the assay plate. Following the sample incubation, the assay plate is washed and a labeled detection mAb solution is added. Following the detection reagent incubation, the plate is washed, buffer is added, and the plate is read. This assay was also performed without an acidification step, where the samples were diluted in assay buffer prior to sample addition to the assay plate.

For the assay performed with a concurrent addition of analyte and detector (C-AD), the samples were first diluted in an acidic solution and allowed to incubate. After plate washing, the acidified samples were then further diluted in a basic neutralization buffer containing the labeled detection mAb before addition to the assay plate. Following the sample incubation, the plate is washed, buffer is added, and the plate is read. This assay was also performed without an acidification step, where the samples were first diluted in assay buffer before a subsequent dilution in assay buffer containing the labeled detection mAb, prior to sample addition to the assay plate.

Figure 2A:
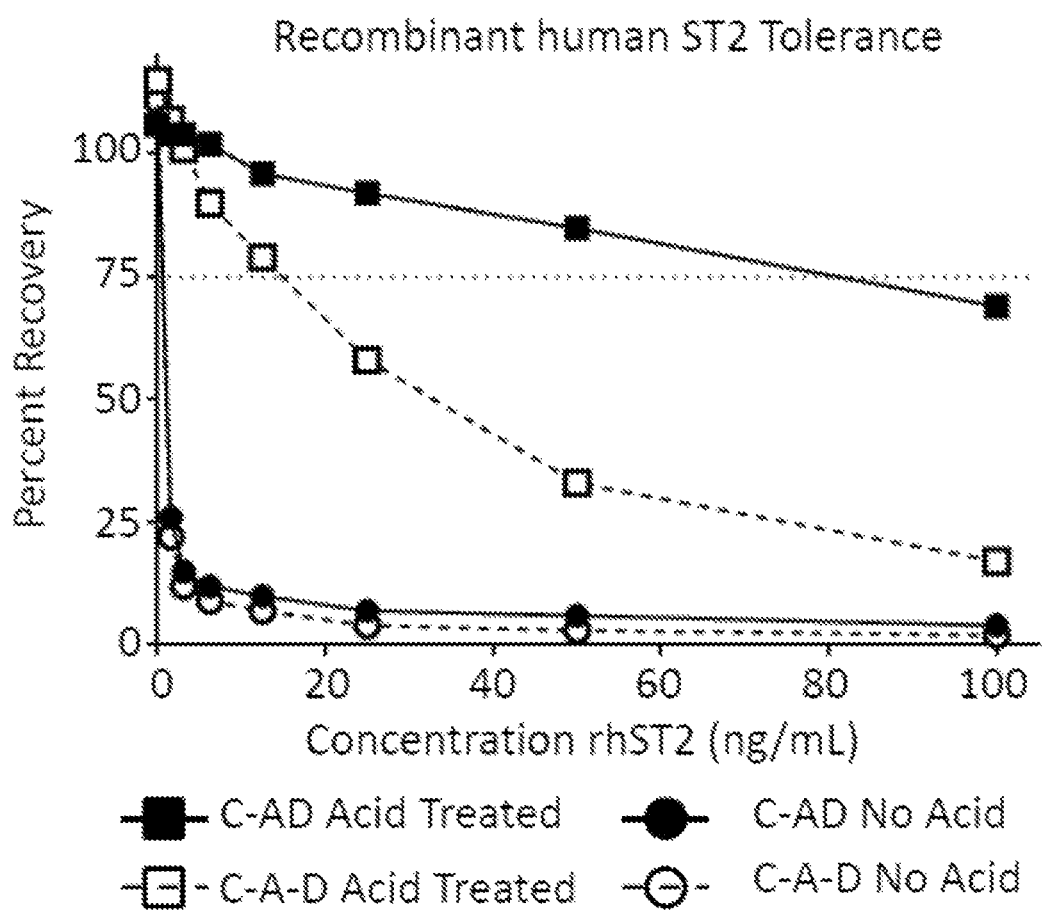
FIG. 2A is a line graph of percent recovery versus concentration of rhST2 (ng/ml). (■) C-AD Acid Treated; (●) C-AD No Acid; (□) C-A-D Acid Treated; (○) C-A-D No Acid.

Recombinant IL-33 at 36 pg/mL was tested in 4 different conditions of the assay, as described above, in the presence of increasing concentrations of recombinant soluble ST2, as indicated in FIG. 2A.

Results

Figure 2B:
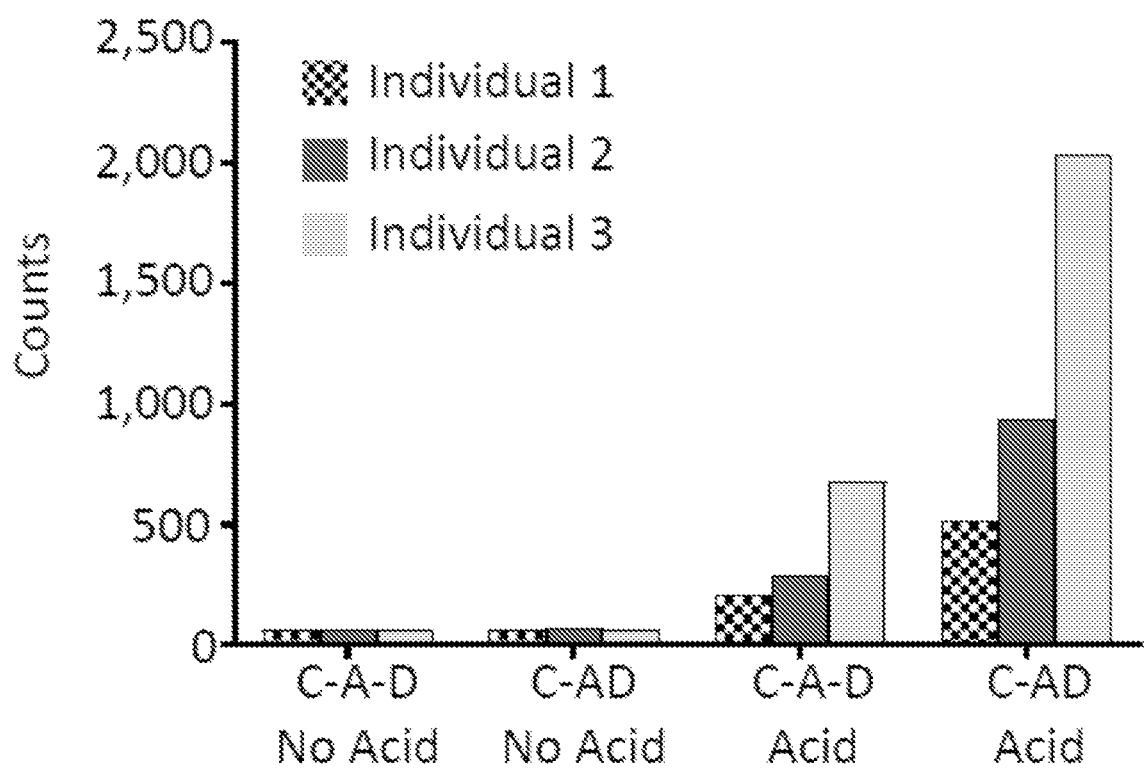
FIG. 2B is a bar graph showing endogenous IL-33 detection in serum from three individuals (Individual 1, Individual 2, and Individual 3) assayed under the indicated conditions: C-A-D No Acid, C-AD No Acid, C-A-D Acid, and C-AD Acid.

Acid treatment is necessary to detect recombinant human IL-33 in the presence of recombinant ST2. Adding an acid treatment step to the C-A-D assay improves ST2 tolerance to ~12 ng/mL, and ST2 tolerance can be improved further to >50 ng/mL by using the C-AD assay format with acid treatment (FIG. 2A). Acid treatment is also necessary to improve detection of endogenous IL-33 in human serum. The detection of endogenous IL-33 is improved using the C-AD assay format when compared to the C-A-D assay format due to the reduction in assay interference from endogenous binding partners (FIG. 2B).

Example III

Precision and Specificity: Endogenous IL-33

Materials and Methods

Assay specificity to IL-33 was confirmed by analyzing 2 different individual serum samples in the C-AD assay with acid treatment as described in example II, tested with and without the addition of excess recombinant human ST2 or 200 µg/mL of an anti-IL-33 antibody in the basic neutralization solution containing the detection reagent.

Two individuals were testing using the C-AD assay with acid treatment as described in example II. The data represents 4 separate replicate determinations performed on 5 separate days.

Results

Figure 3:
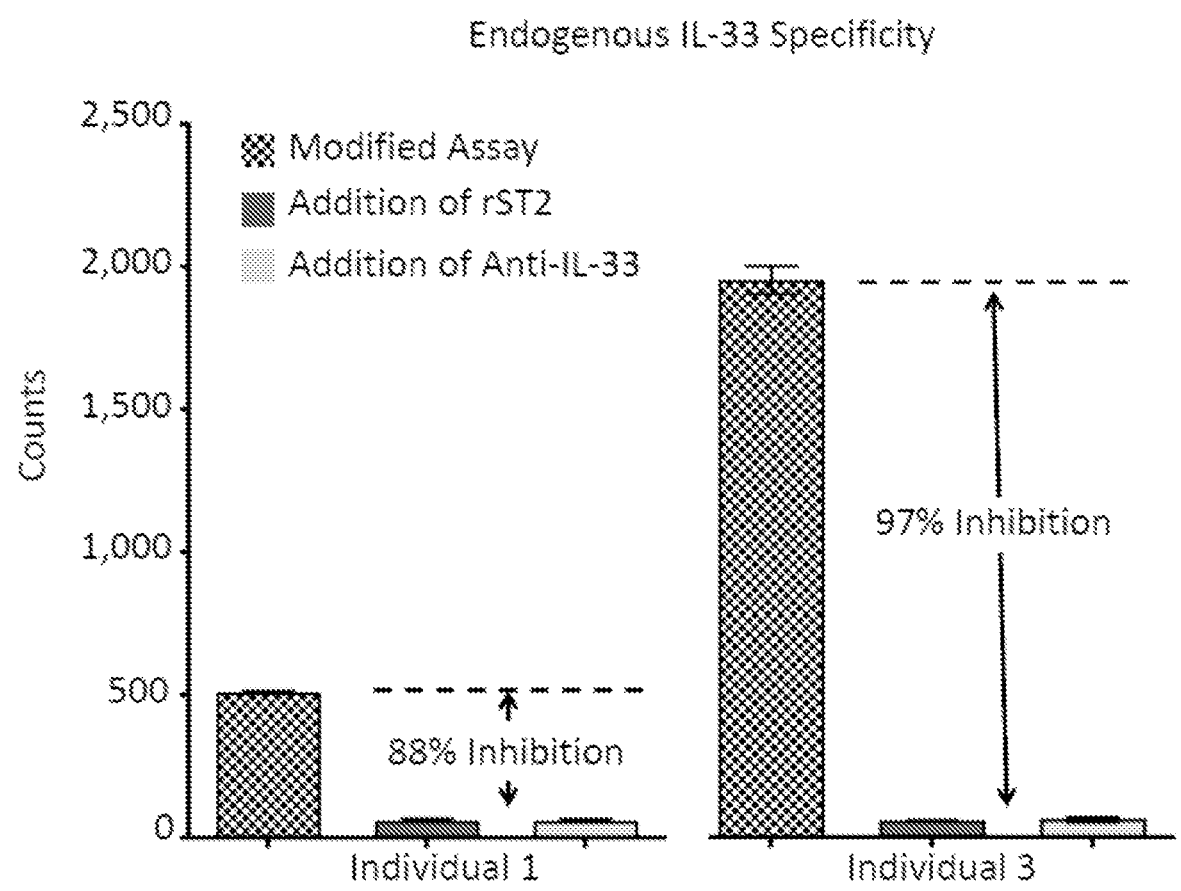
FIG. 3 is a bar graph showing endogenous IL-33 specificity in serum from Individual 1 and Individual 3 using a modified assay, addition of rST2, and addition of an anti-IL-33 monoclonal antibody.

The assay is specific for endogenous IL-33, as the addition of binding partners, e.g. recombinant ST2, or an anti-IL-33 mAb, to the neutralization solution inhibits detection of IL-33. FIG. 3 is a bar graph showing endogenous IL-33 specificity.

Figure 4:
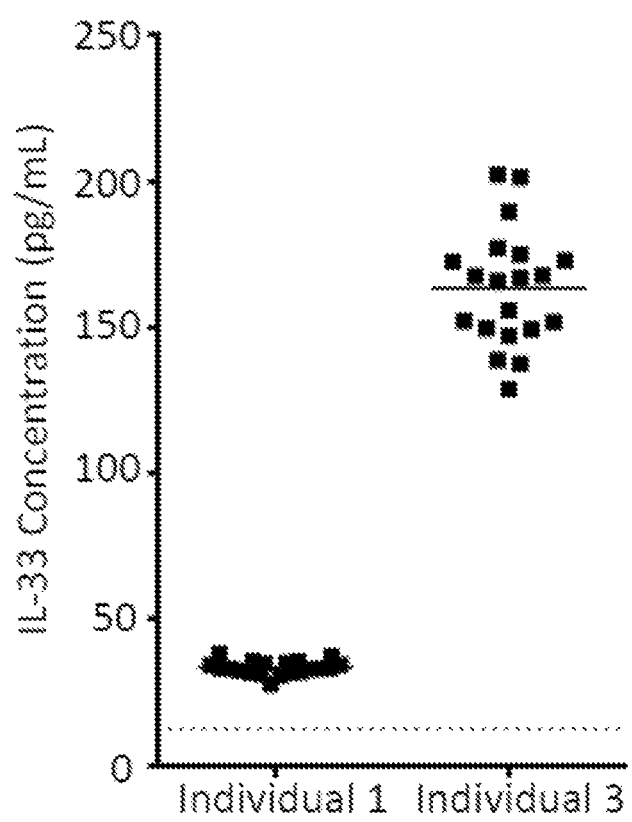
FIG. 4 is a graph of IL-33 concentration (pg/mL) for Individual 1 and Individual 3 after multiple measurements showing that the assay is precise.

The assay demonstrates acceptable precision with a percent coefficient of variation (%CV) of 7.1 and 12.3 for individuals 1 and 3 respectively. FIG. 4 is a graph showing precision of the assay in quantifying endogenous IL-33 in human serum.

Example IV

Detection of IL-33 in the Presence of an Anti-IL-33 mAb (Anti-IL-33 mAb Tolerance)

Materials and Methods

Figure 5:
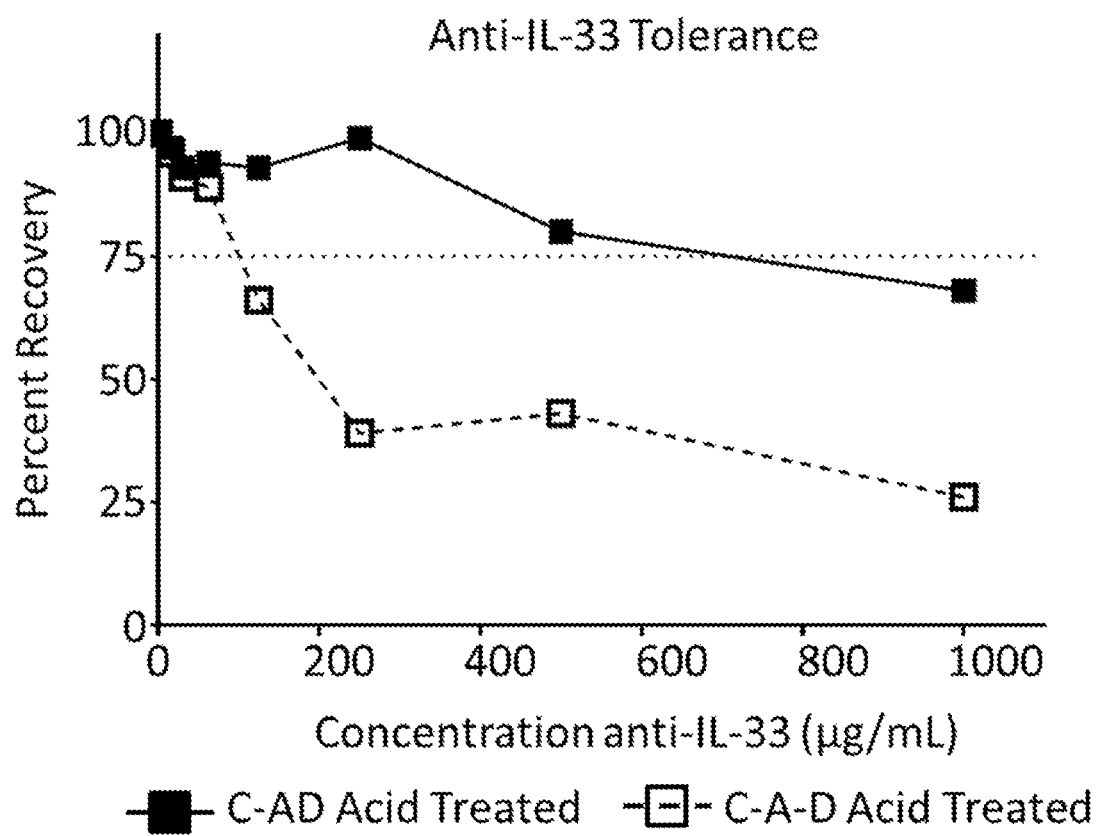
FIG. 5 is a line graph showing the tolerance of the method for detecting IL-33 in the presence of an anti-IL-33 mAb assayed under the indicated conditions: C-AD Acid Treated and C-A-D-Acid Treated.

FIG. 5 is a line graph showing the tolerance of the method for detecting IL-33 in the presence of an anti-IL-33 mAb. Recombinant IL-33 at 90 pg/mL was tested in the C-AD method with acid treatment described in example II, in the presence of increasing concentrations of an anti-IL-33 mAb, as indicated in FIG. 5. The assay was modified by the addition of excess anti-drug mAb and anti-ST2 mAb to the neutralization solution.

Results

Acid treatment is important to detect human IL-33 in the presence of anti-IL-33 mAb. Adding the detection reagent into the neutralization solution, along with the addition of anti-drug mAb and anti-ST2 mAb improves anti-IL-33 mAb tolerance in the assay to >500 µg/mL.

Example V

Endogenous IL-33 Levels in Normal and Diseased Individuals

Materials and Methods 25 individuals each from 4 different populations were purchased from a commercial vendor and were screened for endogenous IL-33 using the assay the C-AD assay with acid treatment as described in example II.

Results

Figure 6:
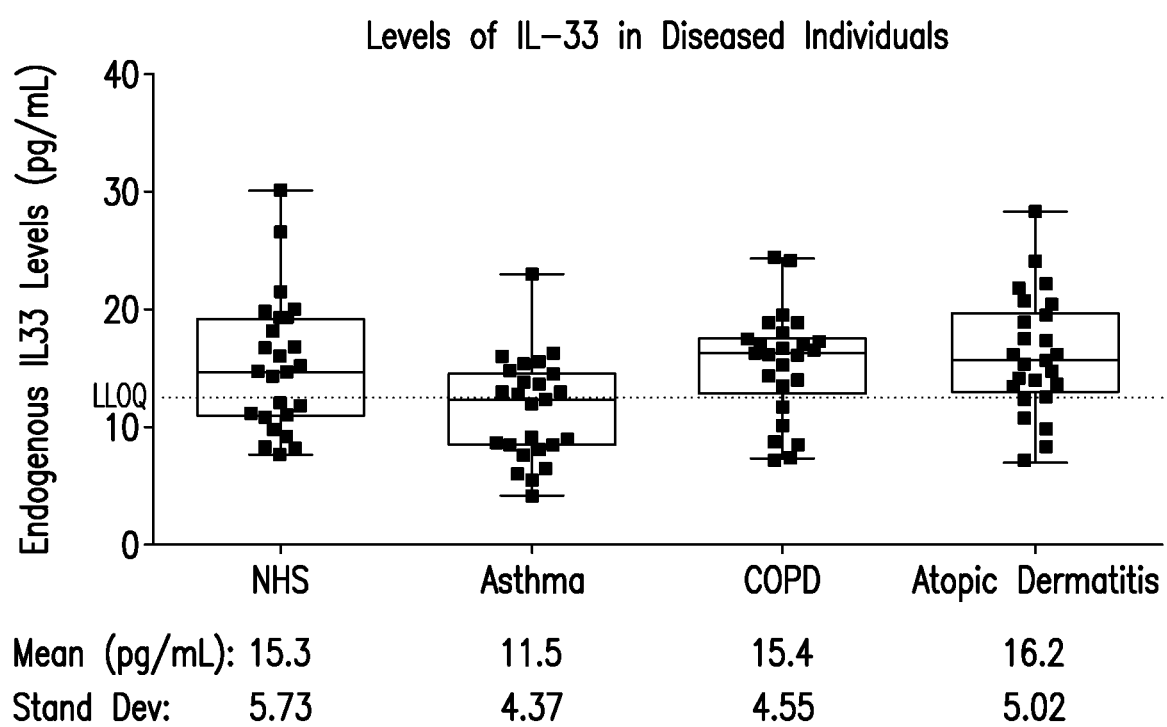
FIG. 6 is a graph of endogenous IL-33 (pg/mL) in serum from normal individuals and individuals with asthma, COPD, and atopic dermatitis. 25 individuals each from 4 different populations were purchased from a commercial vendor and were screened for endogenous IL-33 using the assay the C-AD assay with acid treatment.

FIG. 6 is a graph of endogenous IL-33 (pg/mL) in serum from normal individuals and individuals with asthma, COPD, and atopic dermatitis. All tested individuals resulted in an IL-33 concentration below 31 pg/mL.

Example VI

Humanized Mouse Data

Materials and Methods

Humanized IL-33 mice were treated with house dust mite (HDM) over a 15 week period as a model of human respiratory disease. An exemplary humanized IL-33 mouse is disclosed in US Patent Publication No. 20170311580, which is incorporated by reference in its entirety. Samples were tested in a modified version of the C-AD assay with acid treatment as described in example IV.

Results

Figure 7A:
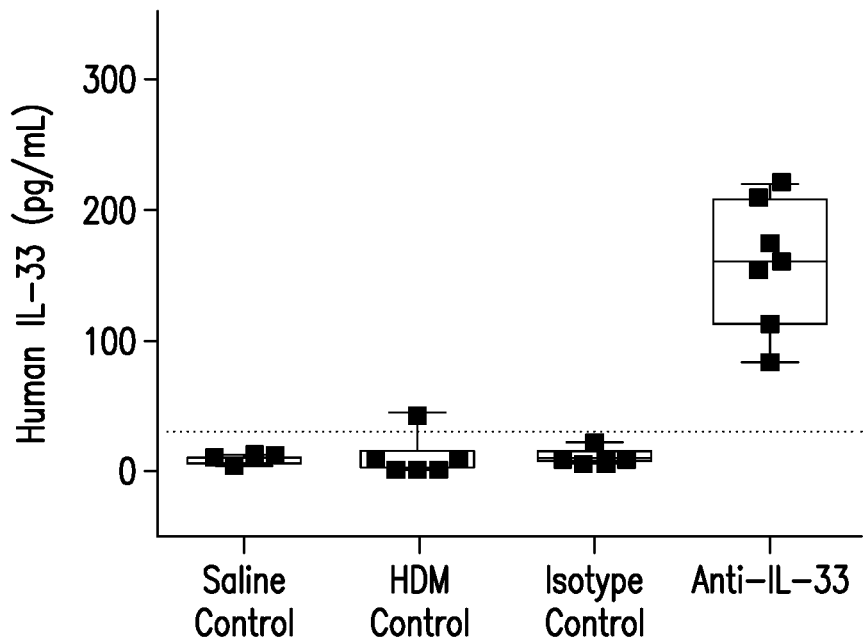
FIGS. 7A and 7B are graphs showing human IL-33 (pg/mL) from the treated and control mice.
Figure 7B:
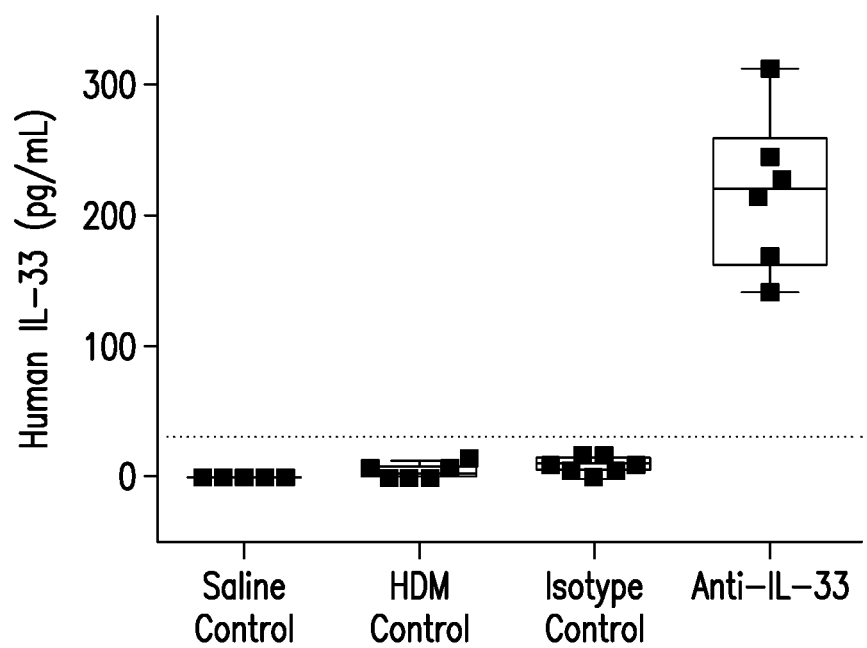

FIGS. 7A and 7B show human IL-33 (pg/mL) from the treated and control mice. Saline, HDM treated, and Isotype controls showed similar levels of human IL-33 at the end of treatment. Mice dosed with Anti-IL-33 monoclonal antibody showed a marked increase in serum IL-33 levels.

A total human IL-33 assay has been developed that has a sensitivity of 12.5 pg/mL in neat serum. Collectively the data show that an acid treatment step is important for removing IL-33 endogenous binding partners. The addition of the detection antibody to the neutralization solution improves recombinant/endogenous ST2 tolerance. The assay has demonstrated specificity for endogenous human IL-33. HDM treated mice dosed with an anti-IL-33 antibody show an increase in human IL-33 due to bound target assuming the half-life of the drug, while the HDM and Isotype controls appeared to remain at baseline.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method of decreasing IL-33 assay interference, comprising the steps of:
   acidifying a sample comprising blood, serum, or plasma to a pH of 3 to 5 to dissociate IL-33 from IL-33 complexes in the sample, wherein acidifying the sample includes adding a denaturing agent to the sample;
   subsequently neutralizing the acidified sample with a buffered basic solution comprising a detection reagent, wherein the detection reagent does not compete for binding to IL-33;
   adding a capture reagent to the sample; and
   detecting the detection reagent, wherein the quantity of detection reagent detected correlates to the quantity of IL-33 in the sample.

2. The method of claim 1, wherein the sample is from a subject that was administered an IL-33 drug product.

3. The method of claim 2, wherein the IL-33 drug product comprises an anti- IL-33 antibody.

4. The method of claim 1, wherein the IL-33 complex comprises IL-33 non-covalently bound to a protein.

5. The method of claim 4, wherein the protein is an endogenous serum protein.

6. The method of claim 4, wherein the protein is ST2 or an IL-33 binding fragment thereof.

7. The method of claim 4, where the protein is an anti-IL-33 antibody or an IL-33 binding fragment thereof.

8. The method of claim 1, wherein the sample is acidified for 5 to 60 minutes.

9. The method of claim 1, wherein the detection reagent comprises an anti-IL-33 antibody conjugated to a detectable label.

10. The method of claim 1, wherein the detection reagent comprises a detectable agent selected from the group consisting of a rare transition metal particle, a fluorophore, a chromophore, a quantum dot, and noble metal nanoparticles.

11. The method of claim 1, wherein the detection reagent is labeled with ruthenium.

12. The method of claim 1, wherein the capture reagent is conjugated to solid support.

13. The method of claim 1, wherein the capture reagent is biotinylated.

14. The method of claim 1, wherein the sample is acidified with acetic acid.

15. The method of claim 1, wherein the buffered basic solution further comprises a blocking agent that inhibits IL-33 complex formation, and wherein the blocking agent does not compete for binding to IL-33.

16. The method of claim 15, wherein the blocking agent is an anti-ST2 antibody.

17. The method of claim 1, wherein the capture reagent is added to the sample during the acidification step.

18. The method of claim 1, wherein the blocking agent is added to the sample after the neutralizing step.

19. The method of claim 1, wherein the capture reagent and the blocking agent are added to the sample after the neutralizing step.

20. The method of claim 1, wherein the sample is obtained from a subject diagnosed with or suspected of having an inflammatory disease or disorder.

21. The method of claim 1, wherein the sample is obtained from a subject diagnosed with or suspected of having asthma, chronic obstructive pulmonary disease, or atopic dermatitis.

22. The method of claim 1, wherein the solid support is an electrochemiluminescence platform.

23. The method of claim 1, wherein the quantity of IL-33 is determined by correlating the amount of detected detection reagent to a predetermined reference standard.

24. The method of claim 1, wherein the denaturing agent is urea.

25. A method of quantifying interleukin-33 in a serum sample, comprising the steps of:
   acidifying the serum sample to a pH of 3 to 5 to dissociate IL-33 complexes in the sample, wherein acidifying the serum sample includes adding a denaturing agent to the serum sample;
   neutralizing the acidified sample with a buffered basic solution comprising an anti-human IL-33 antibody labeled with a detectable label;

adding the sample to an avidin-coated solid support comprising a biotinylated anti-human IL-33 antibody; and detecting the detectable label on the avidin-coated solid support, wherein the quantity of detectable label detected correlates to the quantity of IL-33 in the sample.

26. The method of claim 25, wherein the solid support is a streptavidin-coated electrochemiluminescence platform.

27. The method of claim 25, wherein the detectable label is ruthenium.

28. The method of claim 25, wherein the buffered basic solution further comprises an anti-human ST2 antibody.

29. The method of claim 25, wherein the denaturing agent is urea.

30. The method of claim 28, wherein the anti-human ST2 antibody is present in an amount sufficient to reduce ST2 binding to IL-33 in the sample .

\* \* \* \* \*